United States Patent [19]
Weaver

[11] 3,948,731
[45] Apr. 6, 1976

[54] METHOD AND APPARATUS FOR MEASURING REACTANT CONCENTRATIONS AND QUANTITIES

[75] Inventor: James C. Weaver, Wayland, Mass.

[73] Assignee: Massachusetts Institute of Technology, Cambridge, Mass.

[22] Filed: Oct. 24, 1974

[21] Appl. No.: 517,422

[52] U.S. Cl............................................ 195/103.5 R
[51] Int. Cl.²........,.............................. C12K 1/04
[58] Field of Search............ 195/103.5 R; 23/230 B

[56] References Cited
UNITED STATES PATENTS

| | | | |
|---|---|---|---|
| 3,694,163 | 9/1972 | Sherelis | 195/103.5 R |
| 3,838,034 | 9/1974 | Groves | 195/103.5 R |

Primary Examiner—A. Louis Monacell
Assistant Examiner—C. A. Fan
Attorney, Agent, or Firm—Arthur A. Smith, Jr.; Paul J. Cook; Martin M. Santa

[57] ABSTRACT

A method and apparatus is provided for determining the concentration or quantity of substrate molecules by monitoring directly the concentration and/or the quantity of vaporous byproduct produced from the selective reaction of the molecule catalyzed with a known amount of an enzyme or a microorganism. The apparatus comprises a membrane permeable to the vaporous by-product, a known amount of microorganism or an enzyme immobilized adjacent to the membrane, means for introducing a liquid sample into contact with the microorganism or enzyme and means for measuring the amount of vaporous by-product passing through the membrane. A mass spectrometer located adjacent the membrane surface having the immobilized enzyme or microorganism is suitable for measuring the amount of vaporous by-product passing through the membrane. The process is conducted by first calibrating the apparatus with a known concentration of substrate and thereafter contacting a sample containing an unknown concentration of substrate with the enzyme or microorganism.

8 Claims, 2 Drawing Figures

METHOD AND APPARATUS FOR MEASURING REACTANT CONCENTRATIONS AND QUANTITIES

The invention herein described was made in the course of work performed under a grant from the national Institute of Health.

BACKGROUND OF THE INVENTION

This invention relates to a method and apparatus for measuring the concentration of a substrate the reaction of which is catalyzed with a microorganism or an enzyme to form a vaporous product or for measuring the concentration of a microoganism or an enzyme which catalyzes the reaction of a substrate to form a vaporous product or for measuring the concentration of an inhibitor of a reaction catalyzed by a microorganism or enzyme.

Enzymes and certain microorganisms such as bacteria or yeasts are known to be selective in catalyzing a reaction involving a specific substrate. Based upon this property, these materials have been employed in a wide variety of detection tecniques to determine the presence of and the concentration of the substrate. For example, enzymes and microorganisms have been employed in colormetric reactions wherein the reaction product has a different color than the starting material and the degree of color change is measured by light absorbence. This measurement then can be related to the concentration of the reactant based upon a prior-obtained calibration curve. It is emphasized that such colorimetric determinations are primarily measurements of the accumulation of reaction product and thereby measure the time integral of the reaction rate rather than the rate directly. In addition, biochemical sensors have been employed for determining the concentration of the molecules involving the use of a reference electrode and a biochemical electrode whereby change in potential is measured and this change is correlated to the concentration of the molecule. The biochemical electrode is intimately contacted with an enzyme or bacteria which enzyme or bacteria reacts selectively with the molecule being surveyed to cause a change in the potential between the biochemical electrode and the reference electrode. The use of these biochemical sensors is limited since they require the use of electrodes adapted to measure the presence of a specific ion generated during reaction are subject to interference from the same ions already present in a sample structure. Furthermore, they must be used in conjunction with an electrolyte, which electrolyte will differ depending upon the type of electrode and type of reaction being employed. Thus, these biochemicals sensing systems are undesirably limited in that only an undesirably limited number of reactants can be monitored therewith. Furthermore, because of their bulk and because of the need for employing an electrolyte, a relatively large volume of reactant is necessary in order to obtain accurate results.

Another common method for measuring the concentration or quantity of various compounds is by means of mass spectroscopy wherein the sample to be analyzed is vaporized, ionized and subjected to an electrical or magnetic field to separate the ions on the basis of mass. While this method has wide application and is considered to be a sensitive and accurate technique, it has limitations particularly as applied to the measurement of relatively high mass molecules. This is because there is some degradation and fragmentation of relatively high mass materials during ionization resulting in a reduced detection of the material present. Also, a significant limitation in the measurement of large mass molecules is due to the complexity of their mass spectra that arises from fragmentation. Thus direct mass spectroscopy of a mixture of large mass molecules usually yields an unuseable superposition of complicated mass spectra, so that identification and measurement of the large mass molecules in mixtures is difficult and often impossible. For this reason it is usual to precede mass spectroscopy of mixtures by one or more separation techniques, particularly gas chromatography. Even then, however, due to overlapping gas chromatography peaks and fragmentation problems, identification and measurement can be ambiguous. In some prior art processes it is undesirable to allow $H_2O$ to be present in the gas chromatograph carrier gas since it enters, in sensitive measurements, in a large, unfavorable ratio to the molecule to be measured.

Furthermore, attempts to increase resolution of a mass spectrometer to improve selectivity in measurements results in an undesirable reduced transmission of the material being measured.

It would be highly desirable to provide biochemical sensing apparatus which could be used to detect the concentration of a wide variety of molecules. Furthermore, it would be highly desirable to provide a biochemical sensing apparatus which does not require the present of an electrolyte and for which small volumes of samples such as physiological fluids can be tested to determine the concentration of molecules.

Furthermore, it would be highly desirable to provide a chemical sensing apparatus and a method for its use to be used to measure, in a selective manner and with extreme sensitivity, the concentration of relatively high molecular weight molecules. Also, it would be desirable to provide a means for measuring the concentration and/or quantity of molecules wherein the presence of water does not adversely affect the sensitivity of the measurement.

SUMMARY OF THE INVENTION

This invention provides a method and apparatus for determining the concentration or quantity of molecules by monitoring directly the concentration and/or quantity of vaporous by-product produced from the selective reaction of the molecule catalyzed with a known amount of an enzyme or a microorganism. The apparatus comprises a membrane permeable to the vaporous by-product, a known amount of a microorganism or an enzyme immobilized adjacent to the membrane, means for introducing a liquid sample into contact with the microorganism or enzyme and means for measuring the amount of vaporous by-product passing through the membrane. A mass spectrometer located adjacent the membrane surface having the immobilized enzyme or microorganism is suitable for measuring the amount of vaporous by-product passing through the membrane.

DESCRIPTION OF SPECIFIC EMBODIMENTS

Figure 1:
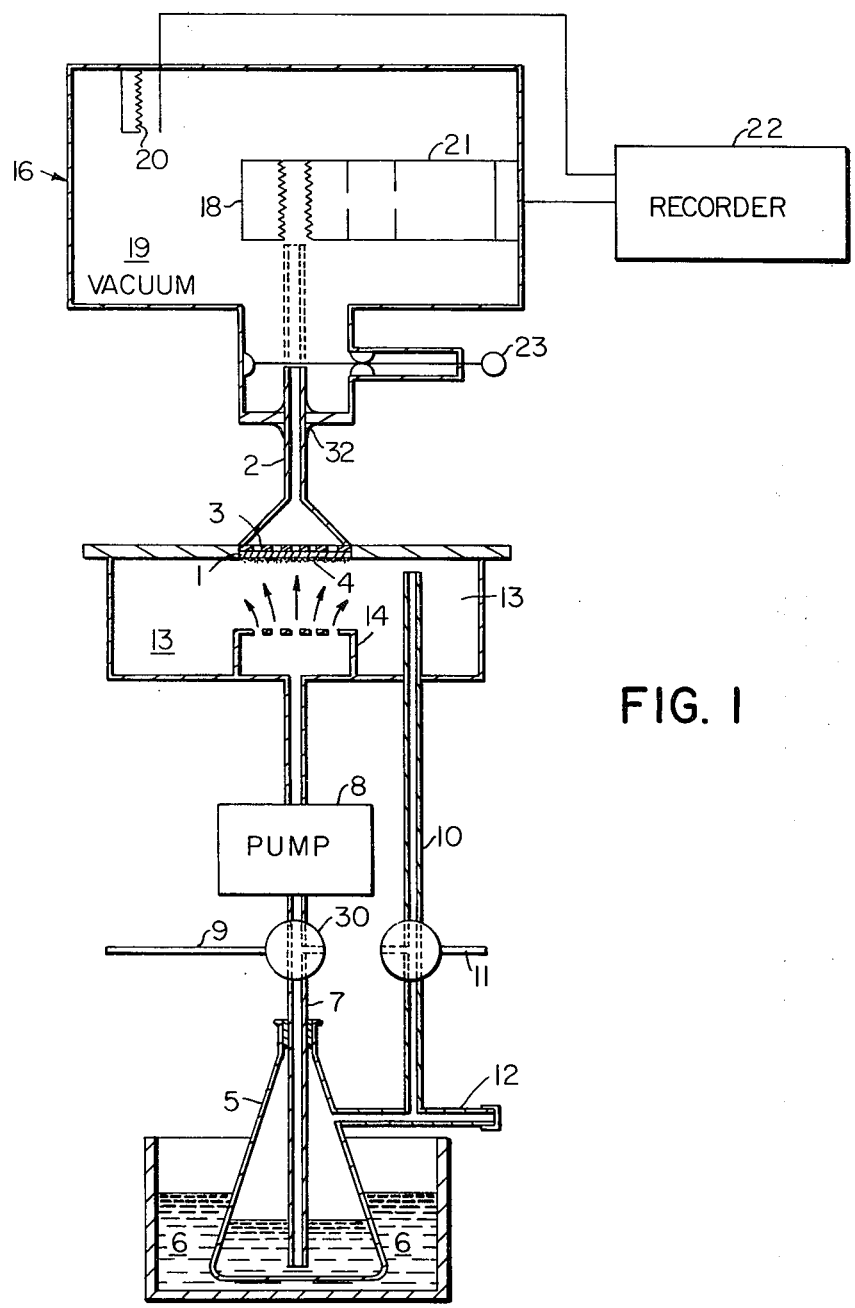
FIG. 1 is an elevational view of an apparatus suitable for practicing this invention.

Referring to FIG. 1, a membrane 1 such as a polysiloxane having polyester fibers on its surface and which is permeable to carbon dioxide is sealed to transfer tube 2 and is supported by perforated plate 3. An enzyme such as urease is immobilized adjacent to the polyester fibers on the membrane as a layer 4. The sample to be tested is placed in container 5 which, in turn, is placed in a constant temperature bath 6. The container 5 is provided with a sample outlet tube 7 having a pumping means 8 such as a peristaltic pump. A plenum chamber 13 is provided to contact the liquid sample and the immobilized enzyme layer 4. A perforated plate 14 functions to distribute the liquid sample evenly with mixing in contact with the enzyme layer 4. The sample delivery system is provided with means for degassing the sample including an inert gas inlet 9 connecting a source of inert gas (not shown) to the sample outlet tube 7, return tube 10 and gas outlet tube 11. Sample can be delivered conveniently to container 5 by injection through stoppered tube 12.

The apparatus for measuring the vaporous by-product of the enzyme-catalyzed reaction includes a mass spectrometer, generally indicated by 16, and a vapor transfer tube 17. The mass spectrometer 16 includes an ionizer 18, a vacuum chamber 19, means for forming a vacuum (not shown), a vacuum gauge 20, a mass filter 21 and recording means 22 for recording at desired mass peaks and pressure in the vacuum chamber 19. For use in the present invention, the mass spectrometer is provided with a sliding plate 23 which functions as a valve between the transfer tube 2 and the vacuum chamber 19. The plate 23 has appropriate sealing means to prevent communication between the chamber 19 and transfer tube 2 when the plate 23 is in the closed position.

The operation of the apparatus of this invention will be described with reference to the use of immobilized urease and an aqueous liquid containing urea. The urease catalyzes the degradation of urea to ammonia and carbon dioxide. In the process of this invention, it is preferred to monitor the carbon dioxide rather than the ammonia product from urea in aqueous solution to obtain accurate results since ammonia has a greater affinity for water than does carbon dioxide and therefore, will not permeate the membrane as well as carbon dioxide. Initially, the sample is degassed to remove much of the carbon dioxide dissolved therein. An inert gas such as nitrogen is introduced into tube 9 by opening three-way valves 30 and 31 so that the nitrogen passes through the sample, tube 12 and out tube 11. Thereafter three-way valves 30 and 31 are positioned so that when pump 8 is operated, sample will move from container 5 through tube 7, plenum chamber 13 to contact the immobilized enzyme 4 and then be recycled through tubes 10 and 12 to return to container 5. In this prototype only a fraction of the urea in the sample is converted to ammonia and carbon dioxide. However significant carbon dioxide and some ammonia permeate the polysiloxane due to the proximity of the enzyme to the membrane which permits measurements of urea as low as about $2\times10^{-6}$ M. Prior to contacting the sample and enzyme, valve 23 is opened and transfer tube 2 is raised to a point adjacent the ionizer 18 through vacuum seal 32. During reaction of the urea, the carbon dioxide and ammonia permeate the enzyme layer, the polysiloxane membrane 3 and enter transfer tube 2 through the perforation in plate 3 and pass into the ionizer 18 through transfer tube 2. The gas molecules are ionized, filtered by a quadrapole mass filter and counted in any manner well known in the art of mass spectroscopy.

Figure 2:
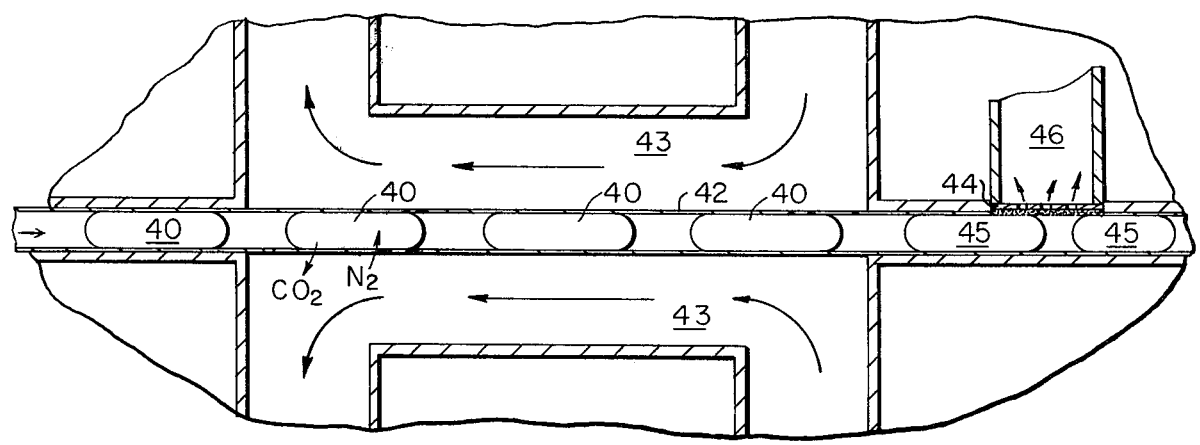
FIG. 2 is a schematic diagram illustrating a means for practicing this invention on a semi-continuous basis.

Referring to FIG. 2, a plurality of liquid samples 40 interspaced by a gas are sequentially introduced into a tubular passage 41 by any means well known in the art, such as is disclosed by U.S. Pat. No. 2,797,149 to Skeggs which is incorporated herein by reference. The samples 40 are pumped through a tubular membrane 42 having its outer surface in contact with a chamber 43 containing an inert gas such as nitrogen. The samples 40 are degassed while being passed through membrane 42 and, thereafter, are passed into tube 43. Tube 43 contains a membrane having a nearby immobilized enzyme 44. When the degassed sample 45 contacts the enzyme, any substrate therein is reacted to form a vaporous by-product which permeates the membrane 44 into transfer tube 46 to a gas detecting means (not shown). When the diameter of tube 43 is small, i.e. less than about 100 microns, the enzyme can be immobilized adjacent to the membrane 44 but located not on the membrane surface but on the inner surface of tube 43 approximately diametrically opposite the membrane 44.

This invention provides substantial advantages over the prior art processes and apparatus for measuring the concentration or quantity of molecules. The apparatus of this invention is adapted to include means for measuring the presence of virtually any volatile molecule which can be passed through a membrane and therefore the apparatus is not limited for use with only a specific substrate or class of substrates. Also, the apparatus of this invention is capable of measuring indirectly the concentration of a wide variety of compounds extremely sensitively and accurately. Furthermore, the apparatus of this invention does not require the use of fluids having a specific chemical composition to perform its function. Thus, all that is required is that the physical and chemical make-up of the surrounding fluid permits the enzyme or microorganism to catalyze the reaction with the reactant being tested. Furthermore, since the apparatus of this invention does not require that the reaction catalyzed by the enzyme or microorganism form a particular ion or class of ions, the particular type of enzyme or microorganism employed is not limited. Thus, any enzyme or microorganism capable of catalyzing or entering into a reaction with the substrate to form a vaporous by-product can be employed in this invention.

Further, this invention does not require a complete mass spectrum since relatively simple vaporous molecules are identified and measured by the mass spectrometer. This is in contrast to the prior art in which the molecules of interest are examined directly, with well known complicated fragmentation patterns which usually require both a preceding sample separation technique such as gas chromatography and/or computer processing of the fragmentation pattern for probable identification of the molecule.

The enzyme or microorganism is "immobilized" so that it is retained on the surface of the membrane or adjacent the membrane. It is not necessary that the microorganism or enzyme be retained in the membrane for an indefinitely long period. All that is necessary is that it be retained sufficiently long so that any diffusion thereof away from the membrane occurs over a period of time much longer than the period of time necessary to obtain the vapor concentration readings when the enzyme or microorganism is contacted to the liquid being tested. Generally the period of time necessary to obtain the vapor concentration readings is less than about one minute and more particularly less than about one minute when employing a mass spectrometer.

Presently, there are available a wide variety of techniques for immobilizing a microorganism or an enzyme. Nonlimiting exemplary techniques include crosslinking an enzyme with a dialdehyde such as glutaraldehyde, coupling the enzyme or microorganism to an acrylamide polymer or copolymer such as with diazotization linkage or by physically entrapping the microorganism or enzyme in a gel, or with another nearby membrane, such as dialysis membrane. These and other techniques for immobilizing the microorganism or enzyme are well known in the art and need not be described in detail herein.

Any available enzyme involving a volatile product or substrate, whether naturally occurring or synthetically produced and whether or not in a pure form can be employed in the present invention. Representative suitable specific enzymes are phosphopyruvate carboxylase, alcoholdehydrogenase, catalase, urease, pyruvate decarboxylase, lysine decarboxylase, acetylcholinesterase, histidine decarboxylase, uricase, acetate kinase, oxalate decarboxylase or the like. Representative suitable microorganisms are yeasts, fungi, the anaerobic bacteria and aerobic bacteria which can be employed either or with can be used to measure substrates in liquid, gases or liquids saturated with gas. Representative suitable microorganisms include *Escherichia coli*, *Bacillus substillis*, *Clostridium sporogenes*, *Klebsiella aerogenes*, *Pseudomonas* species, *Candida* species, *Saccharomyces* species, Fungal spores such as from *Asperigillis niger*, *Actinomyces* species. .

In one aspect of the present invention, more than one membrane, each having a different microorganism or enzyme can be employed. The arrangement has the advantage that it can be employed to determine the concentration of two different types of molecules in the same or in different fluids.

Furthermore, the membrane can be associated with more than one enzyme or microorganism. For example, when associated with two enzymes, one enzyme catalyzes a first reaction with the evolution of a first reaction product and this product enters into a second reaction catalyzed by a second enzyme to form a vaporous by-product. For example, lactate dehydrogenase and pyruvate decarboxylase can be included with the membrane to first catalyze the reaction of lactate to pyruvate. Thereafter the pyruvate decarboxylase converts pyruvate to vaporous carbon dioxide.

Also two or more enzymes catalyzing reactions yielding different vaporous products can be associated with the membrane. For example, urease and alcoholdehydrogenase can be included with the membrane to measure urea and NADH respectively, since urease catalyzes the reaction of urea to form $CO_2$ and alcoholdehydrogenase catalyzes NADH to form ethanol.

The invention described herein can be practiced in at least two distinct configurations, each with distinct characteristics and advantages.

The first configuration is embodied in the apparatus of FIG. 1 already described, and is characterized by reacting only a fraction of the substrate molecules present in the sample. In this first configuration the invention exhibits time response behavior associated with an unstirred boundary layer near the enzyme layer and also a stirred region further away from the enzyme layer. When substrate is injected there is a brief time delay while substrate is delivered to the plenum chamber containing the enzyme layer and membrane, which is followed by an initial transient and then a steady state in which the mass-spectrometer count rate is nearly constant in time. A response curve to substrate concentration is obtained by summing the changes in steady state count rate associated with changes in substrate concentration. Thus in this first configuration the mass spectrometer count rate is nearly proportional to the reaction rate. This is to be contrasted to the response of the same first configuration if the immobilized enzyme is inactivated and solubilized enzyme is injected after substrate solution is present, since in this case, following an initial transient, the steady state response is a mass spectrometer count rate which increases in time, and represents a time integral of the reaction rate. Further, for a given quantity of active enzyme and the same substrate concentration, in the first configuration a larger count rate signal is obtained with immobilized enzyme than with solubilized enzyme since with immobilized enzyme the entire reaction is located adjacent to the membrane.

The second configuration of this invention is characterized by behavior associated with a sufficiently small plenum chamber, sufficiently small sample flow rates and sufficiently large quantity of enzyme immobilized near the membrane that all or much of the substrate is reacted upon flowing the substrate solution once through the plenum chamber, and furthermore so that all or much of the vaporous product permeates completely the membrane. In this second configuration the mass spectrometer count rate can be a somewhat more complicated function of time. However the time integral of the count rate provides, within a constant factor of counting efficiency of the mass spectrometer, a direct measure of the number or quantity of substrate molecules present in the sample, since much or all of the substate is enzymatically converted to a vaporous product, much or all of which permeates the membrane. This second configuration is thus particularly well adapted to small volume samples or samples containing an extremely low concentration of substrate.

In this second configuration for a given quantity of active enzyme and quantity of substrate, the same integrated count rate is obtained with either immobilized enzyme or solubilized enzyme, but if solubilized enzyme is used there is the disadvantage that fresh enzyme must be used with each substrate sample. There is the further disadvantage that the production of a vaporous product only can be identified with one of several membranes if the enzyme is immobilized onto the membrane rather than being present in solubilized form.

While this invention has been described above with reference to the use of a known amount of an immobilized enzyme or microorganism to determine the concentration of a substrate, the concentration or quantity of enzyme inhibitors can equally well be measured. Further it is to be understood that the process and apparatus of this invention are also useful to determine the concentration or quantity of an enzyme or microorganism while employing immobilized substrate which reacts to form a vaporous product. This can be accomplished easily by contacting a solution of the enzyme or microorganism to be measured with a semipermeable membrane entrapping a solution containing the substrates, or by mixing a solution of the enzyme or microorganism with a solution containing the substrate(s), adjacent a membrane permeable to the vaporous product which membrane is located adjacent a means for measuring the concentration of the vaporous product passing through the membrane. In the case wherein an enzyme or microorganism is measured, the sensitivity is increased since the turnover number is generally considerably greater than one molecule substrate per second per molecule enzyme. Further this invention can also be used to measure a first substrate or enzyme if a reaction is used in which a second substrate is a vaporous substance. In this case the second substrate and either the first substrate or enzyme is present in a known amount, so that with the presence of either the enzyme or the first substrate a decrease in the mass spectrometer count rate of the second, vaporous substrate occurs.

Except in this last case in which a vaporous substrate is used to measure either a non-vaporous substrate or enzyme, it is preferred to conduct the process of this invention in a manner such that any traces of the expected vaporous product are removed from the system prior to conducting the reaction with the substrate. Thus, it is preferred to degassed the sample prior to contacting it with the enzyme or the microorganism. Furthermore, it is preferred that the vapor detecting means be employed in a vacuum in the absence of the desired vaporous product. By operating in this manner, any measurement of vapor product other than that produced as a result of the reaction of the substrate is substantially or completely eliminated. Of course, it is possible to conduct the process of this invention without prior degassing or without employing a vacuum. When operating in this manner, it is necessary to calibrate the instrument in order to measure the background concentration of the vaporous product. Furthermore, it is preferred to conduct the process of this invention in a manner wherein the sample containing the substrate is passed into contact with the immobilized enzyme or microorganism by way of a channel sufficiently small that essentially all of the vaporous product permeates the membrane into the mass spectrometer. It is further preferred in this case to provide sufficient immobilized enzyme or microorganism that essentially all of the substrate is reacted. By operating in this manner, vapor diffusion through the membrane is increased thereby allowing more complete measurement of the vaporous product.

In use, the apparatus is calibrated by measuring the concentration of a vaporous product of the reaction of a known concentration of the molecule being tested. In this manner, a curve is established which relates the vapor concentration measured with the concentration of the molecule being treated. Generally, these curves show an initially linear relationship between vapor measurements and concentration of the molecule which gradually levels off at an asymptote. Once the standard curve for the particular membrane is established, the apparatus can be employed to measure the concentration of a substrate by reading the vapor concentration measured at any portion of the curve other than the asymptote.

The following examples are intended to illustrate the present invention and are not intended to limit the same.

EXAMPLE I

Aqueous samples were analyzed for urea employing the apparatus generally shown in FIG. 1. The gas detecting apparatus comprised an ionizer and a quadrupole mass spectrometer (Extranuclear Laboratories, Inc., Pittsburgh, PA) for counting of the intercepted volatile molecules ($CO_2$). A perforated stainless steel disc containing six holes each with a diameter of about 0.2 cm was used to support the $CO_2$-permeable membrane. This disc provides the main mechanical support against the 1 atmosphere pressure differential between the sample and vacuum. A single piece of $1\mu$ pore size, $10\mu$ thick Nuclepore (General Electric Co.) filter was interposed between the disc and silicone rubber membrane for direct mechanical support of the membrane. The dimethyl silicone rubber membrane (General Electric Membrane Products Div., Schenectady, N. Y.) 0.5 mil $\simeq 1.3 \times 10^{-3}$ cm thick, had a polyester backing which is approximately $5 \times 10^{-2}$ cm thick and onto which the enzyme was immobilized.

Urease was immobilized onto the singly backed dimethyl silicone membrane by a method which consists of three steps: adsorption of the enzyme, fixing with glutaraldehyde, and reaction with any remaining glutaraldehyde by the addition of more enzyme solution.

All the steps of the process were carried out at room temperature. The basic buffer in which everything was mixed, diluted and washed was Tris, 0.1 M, at pH 7.2 with $10^{-3}$ M of EDTA added to precipitate heavy metals.

The process employed was as follows: at T = 24°C, 0.25 ml of a solution of 1 mg of urease (Sigma Chem. Corp., St. Louis, MO, Type VI) per 1 ml of Tris was allowed to incubate on the fiber side of a mounted piece of polyester backed membrane for approximately 1 hour. Then 0.1 ml of a 0.05% solution of glutaraldehyde in Tris was added and allowed to react for one hour. This mixture was then poured off and another 0.25 ml of 1 mg/ml urease was allowed to incubate on the membrane for one hour. This was then rinsed off with a stream of Tris in order to remove all excess enzyme and reagent. The coated membrane was then stored in Tris at 4°C.

In order to calibrate the apparatus, an initial sample injection was made into a circulating solution of Tris buffer at T=30°C such that amount of urea was $10^{-3}$ M. The time required for 63% of the change from the initial to final steady state mass spectrometer count rate was about 4 sec. A subsequent total of five injections to a maximum amount of urea of $2.5 \times 10^{-2}$ M was reached. A comparison of this response curve of mass spectrometer count rate as a function of sample concentration to a linear or proportionate fit shows that the response is flattening below the $K_M$ for solubilized enzyme in other buffers (for example, $K_M$, solubilized = $3 \times 10^{-3}$ M in maleate buffer). At the end of this first run solubilized urease was injected as a further test, and the mass spectrometer count rate exhibited a transient followed by a linear increase in time as in the previous runs without immobilized enzyme. More detailed data was taken over a wider range on a similarly prepared membrane (see Example II), and shows both a linear response below $10^{-3}$ M and the flattened response above $10^{-3}$ M. After the calibration curve is obtained the apparatus can be used to measure urea in the range $1 \times 10^{-3}$ M to $2.5 \times 10^{-2}$ M.

EXAMPLE II

With a new urease membrane prepared using the technique described in Example I and under the same conditions of pH and temperature, a second run with an aqueuos solution of urea was made. Again stepwise injections of urea were made, this time starting at urea $= 10^{-8}$ M but the counting efficiency and background $CO_2$ level of the prototype were such that a $CO_2$ vapor response was first seen at urea $\simeq 2\times10^{-6}$ M.

The shape of the response of the mass=44 signal for $CO_2$ with time was qualitatively the same as in the run described in Example I. Following urea injection there was a 20 second delay until the mixing slug of relatively concentrated urea reached the membrane, whereupon a sharp transient increase in count rate was seen. This was followed by a dip and then a small increase to a fairly steady count rate. This behavior is attributed to mixing of the injected sample until a new, uniform concentration of urea is reached. The final steady count rate is used in plotting the response curve, which gives the total (summed) response as a function of total urea concentration. The response time to 63% of the final counting rate was about 6 sec. This response curve consists of eleven points and shows both a linear region for [urea] below $10^{-3}$ M and a leveling off above $10^{-3}$ M, and is consistent with the more limited run of Example I. This saturation behavior is furthermore consistent with the behavior of enzyme catalyzed reactions. After this response curve is obtained the apparatus can be used to measure urea from a concentration of $2\times10^{-6}$ M to about $1 \times 10^{-1}$ M.

EXAMPLE III

Employing the apparatus shown in FIG. 1, a run was made in which the enzyme was alcohol dehydrogenase or ADH which catalyzed the reaction of acetaldehyde and NADH to ethanol and NAD with NADH the unknown substrate and ethanol the volatile product. In this experiment acetaldehyde was initially introduced in excess to give an approximately constant concentration of $5.5\times10^{-3}$ M throughout the experiment. The concentration of acetaldehyde is approximately 7 times its solubilized $K_M = 7.8\times10^{-4}$ M, to allow NADH to be the unknown or sample.

The alcoholdehydrogenase was immobilized by entrapment between a MEM-213 (General Electric Company) membrane and a dialyzer membrane (Type C Technicon Membrane Part No. 105-105-8POIA) with the resultant multilayer membrane being supported on a steel disc containing six perforations of 0.2 cm diameter. The MEM-213 membrane was positioned adjacent the disc.

Samples of NADH were injected with the first several injections also serving as blanks in the sense that the vapor product signal was not seen at very low initial concentrations. The measurement of ethanol at mass 46 as a function of time showed a smooth transient increase characteristic of permeation-diffusion through a membrane until a new steady state counting rate was achieved, with the time to reach 63% of the count rate change being about 80 sec.

The NADH contained ethanol contamination in the amount of approximately one molecule ethanol for every two of NADH. The sample solutions of NADH were not batch degassed of ethanol. Instead the permeability of the same composite membrane to ethanol dissolved in the circulating sample fluid was directly measured at the end of the run by injecting pure ethanol, and found to be $P_{ethanol} = 8.9\times10^{-6}$ cm-sec$^{-1}$. The spurious contamination count rate was then calculated and the vaporous response corrected.

The corrected response curve consists of five points and shows a linear region for [NADH] below about $1\times10^{-4}$ M and a leveling off above $1\times10^{-4}$ M. This saturation behavior is consistent with the behavior of enzyme reactions. Furthermore, as is often the case for immobilized enzymes, the apparent $K_M$ is modified, in this example increased to about $2\times10^{-4}$ M.

More extensive test of the permeability of the MEM-213 membrane was made under similar conditions and the permeability was found to be constant over the range for which the concentration of ethanol = $1\times10^{-5}$ M to $5.5\times10^{-4}$ M. After this calibration curve is obtained the apparatus can be used to measure NADH over the concentration range $2\times10^{-5}$ M to $7\times10^{-4}$ M.

EXAMPLE IV

A run was made in which the enzyme was again alcoholdehydrogenase but an entirely different immobilization method was used from that in Example III. In the present example the enzyme was immobilized on the surface, including the surface of pores, of $25\mu$ pore, $110\mu$ thick, Millipore filter (Millipore Corp.) by a flow through technique using glutaraldehyde.

First a solution was prepared which contained 30 mg ADH in 1 ml 0.05 M phosphate buffer, and $10^{-5}$ M EDTA at pH 7.2. This first solution was flowed through the Millipore filter in order to physisorb the enzyme onto the surface, including the pore surfaces. The membrane was then dired for 15 min. A second solution containing glutaraldehyde then was flowed through the filter for 15 min. to immobilize the physisorbed enzyme by crosslinking. The second solution comprising 1 ml of 25% glutaraldehyde dissolved in 17.4 ml of phosphate buffer, 1.8 ml NADH (concentration NADH $10^{-4}$ M), 1.8 ml acetaldehyde (concentration acetaldehyde $8\times10^{-3}$ M, and $10^{-4}$ M EDTA was used to help protect the active site on the enzyme during immobilization. This second solution was applied to the surface of the filter and forced through with a total exposure of 15 min. The filter was then washed several times and stored at 4°C overnight.

Each side of the filter was assayed separately at room temperature by standard spectrophotometric techniques at 340 nm to monitor consumption of NADH. The initial concentration of NADH was $10^{-4}$ M which is approximately $10 K_M$ for the solubilized enzyme.

In the initial assay one side of the filter gave $6\times10^{-2}$ units of activity (unit = $1\mu$ mole substrate-min$^{-1}$), while the other side gave $2\times10^{-1}$ units. The filter was then stored one day at 4°C, and re-assayed with both sides then giving $(2. \pm 0.5)\times10^{-2}$ units of activity.

This filter was then mounted by being sandwiched between a steel disc having six 0.2 cm diameter holes and a nylon mesh having 1 mm spacing.

Acetaldehyde was again initially added ([acetaldehyde]=$1.2\times10^{-3}$ M), and NADH was treated as the sample. Also as in Example III, the NADH was not degassed of ethanol contaminant, and the ethanol permeability was directly measured at the end of the run for this configuration and this data used to correct the signal. After injection of a NADH sample there was a several second time delay followed by a smooth transient response with a time constant of 45 seconds to reach 63% of a final steady mass spectrometer counting rate. After a series of three NADH injections and measurement of the corresponding steady state counting rates the system was rinsed and a second series, this time consisting of five NADH injections, was made. These eight injections provide a response curve which is linear from a concentration of NADH from $3 \times 10^{-5}$ M to $1.6 \times 10^{-3}$ M, and would allow measurement of NADH in this range. As a final test this example was terminated by introduction of $2 \times 10^{-5}$ M ZnCl which is an inhibitor of ADH and is of sufficient quantity that it should be able to completely inhibit the enzyme. The corrected ethanol signal decreased appropriately to zero upon application of the inhibitor.

I claim:

1. Apparatus for measuring the concentration of a substrate in a liquid which substrate reacts to form a vaporous product when contacted with a fixed amount of an enzyme or microorganism or for measuring the concentration of an enzyme or microorganism in a liquid which enzyme or microorganism catalyzes a reaction to form a vaporous product when contacted with a fixed amount of a substrate for the enzyme or microorganism which comprises at least one membrane permeable to said vaporous product, said enzyme or said microorganism being immobilized adjacent said membrane, means for contacting said substrarte with said enzyme or microorganism to produce a vaporous product wherein either (a) the amount of the substrate is fixed when measuring enzyme or microorganism concentration or the amount of the enzyme is fixed or the amount of the microorganism is fixed when measuring the substrate concentration and means for measuring directly the amount of said vaporous product passing through said membrane.

2. The apparatus of claim 1 having a fixed amount of a first microorganism or a first enzyme immobilized adjacent at least one membrane to cause the reaction of a substrate with the attendant formation of a first reaction product and a fixed amount of a second microorganism or a second enzyme adapted to effect a second reaction involving said first reaction product to form said vaporous product.

3. The apparatus of claim 1 adapted to measure the concentration of at least two substrates in a liquid, said apparatus having a fixed amount of at least two materials selected from the group consisting of an enzyme and a microorganism immobilized adjacent at least one membrane wherein each membrane is permeable to a vaporous product of the reaction involving a substrate and one of said materials immobilized adjacent each membrane.

4. A process for measuring the concentration of a substrate in a liquid which comprises calibrating an apparatus suitable for reacting said substrate to form and measure the amount of a vaporous product by contacting a known amount of substrate with a fixed amount of enzyme or microorganism and measuring the amount of vaporous product, said apparatus comprising a membrane permeable to a vaporous product formed when said substrate reacts when contacted with a microorganism or an enzyme, said enzyme or said microorganism being immobilized adjacent said membrane, means for contacting said enzyme or microorganism with said substrate to produce a vaporous product and means for measuring directly the amount of said vaporous product passing through said membrane and thereafter contacting said fixed amount of enzyme or microorganism with a liquid containing said substrate and measuring the amount of said vaporous product passing through said membrane.

5. A process for measuring the concentration of an enzyme or microorganism in a liquid which comprises calibrating an apparatus suitable for effecting a reaction involving said enzyme or microorganism to form and measure the amount of a vaporous product by contacting a fixed amount of a substrate for the enzyme or microorganism with a known amount of said enzyme or microorganism and measuring the amount of vaporous product, said apparatus comprising a membrane permeable to a vaporous product formed when said substrate reacts when contacted with said microorganism or an enzyme, said substrates being immobilized adjacent said membrane, means for contacting said enzyme or microorganism with said substrate to produce a vaporous product and means for measuring directly the amount of said vaporous product passing through said membrane and thereafter contacting a fixed amount of said substrate with a liquid containing said enzyme or microorganism and measuring the amount of said vaporous product passing through said membrane.

6. The apparatus of claim 1 wherein the means for measuring the amount of vapor passing through the membrane comprises a mass spectrometer.

7. The apparatus of claim 2 wherein the means for measuring the amount of vapor passing through the membrane comprises a mass spectrometer.

8. The apparatus of claim 3 wherein the means for measuring the amount of vapor passing through the membrane comprises a mass spectrometer.

* * * * *